[19] United States Patent
Mohan

[11] Patent Number: 5,981,721
[45] Date of Patent: Nov. 9, 1999

US005981721A

[54] POLYENE MACROLIDE SCHIFF BASES, THEIR ALKYL ESTERS AND PROCESSES FOR PREPARING POLYENE MACROLIDE ALKYL ESTER SALTS THEREOF

[75] Inventor: Arthur G. Mohan, Somerville, N.J.

[73] Assignee: Karykion Corporation

[21] Appl. No.: 08/955,414

[22] Filed: Oct. 23, 1997

[51] Int. Cl.$^6$ .......................... C07H 17/04; A61K 31/70
[52] U.S. Cl. ................................. 536/6.5; 514/31
[58] Field of Search ............................... 514/31; 536/6.5

[56] References Cited

U.S. PATENT DOCUMENTS

| | | | |
|---|---|---|---|
| 4,035,567 | 7/1977 | Sipos | 536/4 |
| 4,035,568 | 7/1977 | Schaffner et al. | 536/17 |
| 4,235,993 | 11/1980 | Keseleski et al. | 536/17 R |
| 4,272,525 | 6/1981 | Wright | 424/177 |

FOREIGN PATENT DOCUMENTS

| | | |
|---|---|---|
| 10297 | 4/1980 | European Pat. Off. . |
| 2336397 | 2/1974 | Germany . |
| 03190819 | 8/1991 | Japan . |
| 05059084 | 3/1993 | Japan . |
| 120035 | 11/1983 | Poland . |
| 142848 | 3/1988 | Poland . |
| 9635701 | 11/1996 | WIPO . |

OTHER PUBLICATIONS

Jolanta Grzybowski, et al., *Pol. J. Antibiot.*, (1997), 50(8), pp. 709–711.
Y. Ridente et al., *Fr. Biospectroscopy*, (1996), 2(1), pp. 1–8.
Benjamin J. Costello et al., *J. Chem. Soc.*, Perkins Trans. 1, (1993), (16), pp. 1829–1830.
N.E. Shvinka et al., *Gen. Physiol. Biophys.*, (1991), 10(5), pp. 499–503.
Toru Otake et al., *Antiviral Res.*, (1991), 16(3), pp. 243–255.
Toru Otake, *Yonago Igaku Zasshi*, (1989), 40(3), pp. 373–381.
K.C. Nicolaou et al., *J. Chem. Soc.*, Chem Commun. (1987), (9), pp. 686–689.
Andrzej Grzybowska et al., *Pol. J. Antibiot.*, (1986), 39(7), pp. 1025–1027.
Jolanta Grzybowska et al., *Pol. J. Chem.*, (1984), 58(4–5–6), pp. 599–601.
J.R. Little et al., *Antimicrob. Agents Chemother.*, (1984), 26(6), pp. 824–828.
Barbara Stefanska et al., *Acta Pol. Pharma.*, (1983), 40(2), mpp. 171–174.
Edgar Haenseler et al., *Biochim. Biophys. Acta*, (1983)745(2), pp. 121–133.
V. Notario et al, *J. Gen. Microbiol.*, (1982), 128(4), pp. 761–777.
David J. Giron et al., *J. Interferon Res.*, (1981), 1(4), pp. 581–586.
Tadanobu Takamura et al., *Shinkin to Shinkin*, (1980), 128(4), pp. 761–777.
Michael a. Saubolle et al., *Antimicrob. Agents Chemother.*, (1978), 14(4), pp. 517–530.
Alice Huston et al., *Antimicrob. Agents Chemother.*, (1978), 13(6), pp. 905–909.
Neil I. Goldstein, et al., *J. Antibiot.*, (1977), 30(4), pp. 321–325.
D. Kerridge et al., *Plant Protoplasts (Prog. Int. Symp. Yeast Other Protoplasts)*, 4th (1976) meeting date 1975, 23–38.
Paul B. Fisher et al., *J. Antibiot.*, (1977), 30(1), pp. 118–123.
Paul D. Hoeprich et al., *J. Infect Dis.*, (1976), 134(4), pp. 336–341.
Nobuo Monji et al., *J. Antibiot.*, (1976), 29(4), pp. 438–443.
Paul B. Fisher et al., *J. Antibiot.*, (1975), 28(11), pp. 896–902.
D.P. Bonner et al., *J. Antibiot.*, (1975), 28(2), pp. 132–135.
Harald A. B. Linke et al., *J. Antibiot.*, (1974), 27(3), pp. 155–160.

*Primary Examiner*—Alan L. Rotman
*Assistant Examiner*—Charanjit S. Aulakh
*Attorney, Agent, or Firm*—Mathews, Collins, Shepherd & Gould, P.A.

[57] ABSTRACT

Processes for the preparation of high purity alkyl esters of polyene macrolide antibiotics are disclosed. The processes involve treating an amphoteric polyene macrolide antibiotic with an aldehyde to yield the corresponding Schiff base which is soluble in the reaction medium. The solution is then treated with an alkylating agent in the presence of a hindered tertiary amine as acid acceptor to yield the alkyl ester of the polyene macrolide antibiotic in the form of its Schiff base derivative. Contacting this derivative with water converts the Schiff base derivative to the desired alkyl ester of the polyene macrolide antibiotic which is recovered from the reaction medium.

25 Claims, No Drawings

POLYENE MACROLIDE SCHIFF BASES, THEIR ALKYL ESTERS AND PROCESSES FOR PREPARING POLYENE MACROLIDE ALKYL ESTER SALTS THEREOF

FIELD OF THE INVENTION

The present invention relates to new Schiff base intermediates of amphoteric polyene macrolides, their conversion to alkyl esters and the use of these intermediates in the preparation of polyene macrolide esters and water-soluble salts thereof.

BACKGROUND OF THE INVENTION

This invention relates to alkyl esters of polyene macrolide antibiotics and to convenient and safe synthesis thereof by methods suitable for large scale production.

U.S. Pat. No. 3,945,993 to Schaffner et al. relates to the preparation of esters of Amphotericin B and other amphoteric polyene macrolides by dissolving the polyene macrolide in methyl sulfoxide and diluting with tetrahydrofuran. The resulting suspension is treated with diazomethane to produce the methyl ester. The ester product is then recovered from the reaction mixture by precipitation with ethyl ether.

U.S. Pat. No. 4,035,568, also to Schaffner et al., relates to processes for making Amphotericin B derivatives using diazomethane or diazapropane.

Belgian Patent No. 802,512 relates to another method for synthesis of the methyl ester of Amphotericin B. Aqueous ammonium hydroxide is added to a solution of Amphotericin B in methyl sulfoxide to approximately pH 10. Treatment of this mixture with diazomethane yields the methyl ester.

U.S. Pat. No. 4,035,567 describes another procedure for the preparation of Amphotericin B methyl ester. Amphotericin B is mixed with either dimethylformamide (DMF) or hexamethylphosphoric triamide (HMPA) for a specific time period. Ammonium hydroxide is then added to raise the pH of the mixture above 9 with DMF or above 10 with HMPA. Diazomethane is then added in each case to form the methyl ester.

The use of diazomethane with unprotected Amphotericin B or other amphoteric polyene macrolides to produce the corresponding methyl esters is most often associated with the formation of undesired by-products. These often consist of compounds wherein methylation has occurred at sites in the molecule in addition to the carboxyl function.

U.S. Pat. No. 4,235,993 describes an attempt to limit the formation of these polymethylated Amphotericin B derivatives. Included are several synthetic steps during which the intermediates, namely N-benzylidine Amphotericin B and its methyl ester, are formed. Amphotericin B is dissolved in equal parts of DMF and dimethyl-sulfoxide (DMSO), and benzaldehyde is then added to form the Schiff base, N-benzylidine Amphotericin B. Treatment of this intermediate with diazomethane in tetrahydrofuran (THF) yields the intermediate product, N-benzylidine Amphotericin B methyl ester. Treatment of this intermediate with acids in aqueous medium hydrolyzes the Schiff base and produces the water-soluble Amphotericin B methyl ester salt.

Most of the available procedures to protect an amine block the amino function as an amide or carbamate (see T. W. Greene, "Protecting Groups in Organic Synthesis", J. Wiley Publ., New York, 1981). The FMOC (fluorenylmethylcarbonyl) group has been employed to protect the amino group of Amphotericin B (M. J. Driver et. al., Tetrahedron Letters, 33, 4357–4360 (1992). Diazomethane or methyl iodide with diisopropylethylamine is then utilized to esterify the carboxyl group and the FMOC protecting group is removed in a second reaction. It is unexpected that use of the Schiff base to protect the amino group is possible in the esterification with an alkylating agent since it might be expected that an alkylating agent such as methyl iodide or dimethyl sulfate would alkylate the imino nitrogen forming an N-methyl compound. The major additional advantages of using the Schiff base protecting group are solubilizing of the Amphotericin B by disruption of its amphoteric character and ease of removal of the protecting group by contact with water under relatively mild conditions which do not effect the sensitive groups in the polyene molecule. An additional benefit is the steric interaction of the Schiff base which prevents alkylation of the hydroxyl groups on the glycosamine function.

Amphotericin B is a polyene macrolide antibiotic useful in a variety of applications including human treatment of systemic fungal diseases and agricultural treatment of fungal plant infections. Amphotericin B and its methyl ester have also been shown to have a broad spectrum of antiviral and anticancer activity. The structure of Amphotericin B (AMB) and its methyl ester (AME) are illustrated below:

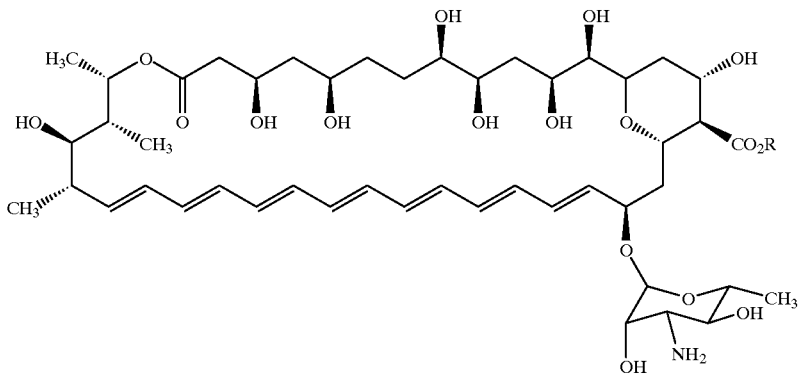

AMPHOTERICIN B: R=H

AMPHOTERICIN B METHYL ESTER: R=CH$_3$

DETAILED DESCRIPTION OF THE INTENTION

The present invention relates to a new and improved process for the preparation of a variety of esters of amphoteric polyene macrolides of improved purity.

As described herein, the process of the invention includes an important step during which key intermediates are formed. The process protects the primary amino group and adjacent hydroxyls on the amino sugar moiety of the amphoteric polyene macrolides. The formation of the Schiff base by treatment with selected aldehydes, such as p-chlorobenzaldehyde also has the additional advantage of solubilizing the polyene macrolide in the solvent of choice, dimethylformamide (DMF). This yields the p-chlorobenzylidine derivatives of polyene macrolides such as Amphotericin B. Protecting the amino group as the Schiff base substantially reduces its reactivity towards the alkylating agent, thus allowing the carboxyl group to be alkylated without affecting the imino nitrogen function.

For example, the esterification of the p-chlorobenzylidine derivative of the amphoteric polyene macrolide is accomplished by treating the DMF solution of the derivative with an alkylating agent (such as an alkyl iodide) in the presence of the hindered tertiary amine such as N,N-diisopropylethylamine. Use of the hindered base to trap the resultant hydrogen iodide which is formed in the esterification process is necessary to avoid quaternization of the tertiary amine by direct reaction of the alkylating agent with the tertiary amine. While this procedure has been previously utilized to esterify the FMOC derivative of an amphoteric polyene, it has now been discovered that the alkylating agent can be applied to the Schiff base of AMB to selectively esterify the carboxyl group without attacking the imino nitrogen as well.

The overall synthetic sequence to prepare the Amphotericin B methyl ester is summarized below:

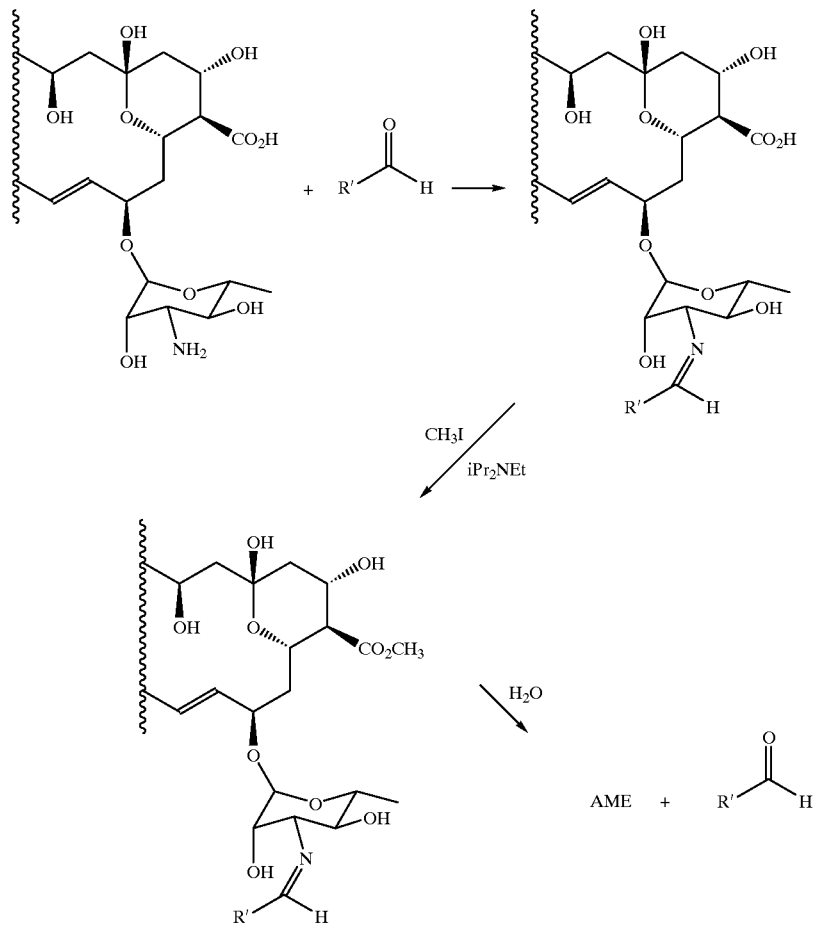

Wherein R' can be for example, an aromatic, aliphatic, or heterocyclic aldehyde.

The invention is not limited to Amphotericin B. It will be appreciated that a variety of other amphoteric polyenes are suitable for use in the invention. These include, but are not limited to, Candicidin, Nystatin, Pimaricin, and Partricin.

Structure of the Aldehyde

The structure of the aldehyde and the solubility properties of the resulting Schiff base are important factors in selecting the optimum aldehyde for the esterification process. It is well known that the formation of a Schiff base by the condensation of a primary amine with an aldehyde or ketone is an equilibrium process:

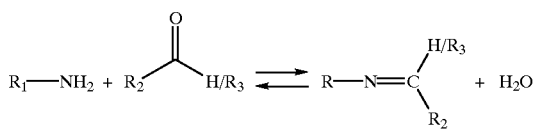

Benzaldehyde and most aromatic aldehydes readily form stable Schiff bases useful in the esterification process. However, an additional requirement of the aldehyde (or ketone) is that the resultant Schiff base be readily hydrolyzed back to the primary amine and the corresponding aldehyde or ketone on contact with a large excess of water.

Trimethylacetaldehyde and p-chlorobenzaldehyde are examples of aldehydes which react readily with primary amines to form stable Schiff bases in high yield. However, on contact with excess water both readily hydrolyze under mild conditions to regenerate the primary amine and the corresponding carbonyl compounds in high yield.

One of the major problems in attempting to esterify AMB and related amphoteric polyene macrolides is the poor solubility in most organic solvents. The zwitterionic character of these molecules is most likely the cause of this problem. In accordance with the present invention, the use of the Schiff base as a protecting group for the amino group has the additional advantage of disrupting the zwitterionic character of the amphoteric polyene thereby substantially increasing the solubility in polar solvents such as DMF, dimethyl sulfoxide (DMSO), dimethylacetamide, and N-methyl-2-pyrrolidone. The solubility improvement provides a convenient test for completeness of the reaction: when all the amphoteric polyene dissolves, the conversion to the Schiff base is complete. Another useful function of the Schiff base as protecting group is a steric effect of hindering hydroxyl groups on the amino glycoside towards reaction with the alkylating agent. Large, bulky aldehydes such as trimethylacetaldehyde or aromatic aldehydes favor this steric crowding effect.

Structure of the Alkylating Agent

A broad range of alkylating agents may be used in the esterification step. For example, alkyl iodides, bromides and chlorides may be effectively utilized. Sulfates such as dimethyl sulfate, and sulfonates such as methyl methanesulfonate, methyl trifluoromethane sulfonate, or methyl p-toluene sulfonate are also capable of producing high conversions to the esters. The particular choice of alkylating agent depends primarily on factors such as reaction rate, isolation conditions and cost, and can be readily determined by those skilled in the art. The structure of the alkyl iodide has been shown to effect the rate of the esterification as shown by the data summarized in Table 1 below.

TABLE 1

Effect of Structure of Alkylating Agent on Esterification Rate*

| RX | % AMB Unreacted | % Ester | Reaction Time* |
|---|---|---|---|
| $(CH_3)_2SO_4$ | None Detected | 88.6% | 0.25 hr |
| $CH_3I$ | 41.7 | 29.0 | 0.5 hr |
| $CH_3I$ | 27.8 | 55.8 | 1.5 hr |
| $CH_3I$ | None Detected | | 24 hr |
| $C_2H_5I$ | 5.92 | 78.6 | 24 hr |
| n-$C_3H_7I$ | 23.0 | 66.5 | 24 hr |

TABLE 1-continued

Effect of Structure of Alkylating Agent on Esterification Rate*

| RX | % AMB Unreacted | % Ester | Reaction Time* |
|---|---|---|---|
| n-$C_4H_9I$ | 32.6 | 49.9 | 24 hr |

*Reactions carried out at 25° C. on the trimethylacetaldehyde-AMB Schiff base.

Structure of the Base

The base of choice to act as acid acceptor in the esterification reaction is preferably a hindered tertiary amine which is a strong base but a weak nucleophile, and thus unreactive towards the alkylating agents. Typical tertiary amines which may be used are N,N-diisopropylethylamine ("Hunigs Base") or 1,8-bis(dimethylamino)naphthalene ("proton sponge").

The combined use of the suitable aldehyde to form the Schiff base and an alkyl halide to effect alkylation has been found to be most suitable for the production of polyene macrolide alkyl esters in large quantities and of high purity. This procedure avoids the use of the extremely toxic and explosive diazomethane or other diazo-alkanes in the alkylation reaction.[1] The use of the ideal Schiff base of the amphoteric polyene macrolide allows esterification with a broad scope of alkylating reagents such as dimethyl sulfate, methyl p-toluene sulfonate, methyl methane sulfonate, methyl trifluoromethane sulfonate, alkyl halides and the like.

[1] See generally Wade, L. G. Jr., Organic Chemistry, p. 1066, Prentice Hall Publishing (New Jersey 1987).

Broadly speaking, the present process comprises, (a) allowing an amphoteric polyene macrolide to react with an aldehyde (for example, p-chlorobenzaldehyde or trimethylacetaldehyde) to yield a corresponding imine derivative (for example, N-p-chlorobenzylidene or 2,2-dimethylpropylidene) which is soluble in polar organic solvents such as DMF or DMSO, (b) esterifying the imine derivative by contacting said imine derivative with an alkylating agent in the presence of a hindered tertiary amine, to yield the corresponding alkyl ester, and (c) contacting the alkyl ester product with water to convert said imine derivative alkyl ester to the desired amino macrolide ester. This product can then be recovered by standard methods.

More specifically, the invention relates to processes for preparing esters of polyene macrolide antibiotics comprising, (a) allowing a mixture containing an amphoteric polyene macrolide antibiotic to react with an aldehyde selected from the group consisting of aromatic, heterocyclic and aliphatic aldehydes to yield the corresponding imine derivative which is soluble in polar organic solvents, (b) esterifying said imine derivative by contacting said imine derivative with an alkylating agent in the presence of a hindered tertiary amine to yield the corresponding alkyl ester, and (c) contacting said alkyl ester imine product with water to convert said alkyl imine ester product to the polyene macrolide alkyl ester product.

Preferred solvents include polar organic solvents such as acyclic and cyclic secondary amides and dialkyl sulfoxides. Suitable solvents include, but are not limited to, dimethylformamide, dimethylacetamide, N-methylpyrrolidone-2-pyrrolidone, and dimethyl-sulfoxide. Preferred alkylating agents include alkyl iodides (such as methyl iodide), alkyl bromides (such as benzyl bromide), and alkyl and aralkyl chlorides. Preferred alkylating agents also include alkyl sulfonates such as dimethyl sulfate, diethyl sulfonate, methyl methanesulfonate, methyl trifluoromethane sulfonate, and methyl p-toluene sulfonate. Preferred hindered tertiary amines include N,N-diisopropylethylamine and 1,8 bis(dimethylamino)-naphthalene. Preferred aldehydes include benzaldehyde and substituted benzaldehydes, acetaldehyde and substituted acetaldehydes, and furaldehyde and substituted furaldehydes.

It will also be appreciated that the amphoteric polyene macrolide may be extracted directly from the fermentation product mixture without isolation and then esterified according the process of the present invention.

The following examples will serve to further typify the nature of the invention but should not be construed as a limitation on the scope thereof, which is defined solely by the appended claims. The following table outlines Examples 1–18.

Summary of Examples

| Example# | Polyene | Aldehyde | Alkylating Agent | Ester |
|---|---|---|---|---|
| 1 | AMB | ClBzH | MeI | Methyl |
| 2 | AMB | Me₃CCHO | MeI | Methyl |
| 3 | AMB | ClBzH | Me₂SO₄ | Methyl |
| 4 | AMB | ClBzH | MeOTs | Methyl |
| 5 | AMB | ClBzH | MeSO₃Me | Methyl |
| 6a | AMB | Me₃CCHO | EtI | Ethyl |
| 6b | AMB | Me₃CCHO | PrI | Propyl |
| 6c | AMB | Me₃CCHO | BuI | Butyl |
| 7 | AMB | ClBzH | BnCl | Benzyl |
| 8 | AMB | ClBzH | MeOTs | Methyl |
| 9 | AMB | ClBzH | Me₂SO₄ | Methyl.AcOH |
| 10 | AMB | ClBzH | Me₂SO₄ | Methyl.HCl |
| 11 | Candicidin | ClBzH | Me₂SO₄ | Methyl |
| 12 | Nystatin | ClBzH | Me₂SO₄ | Methyl |
| 13 | Pimaricin | ClBzH | Me₂SO₄ | Methyl |
| 14 | Partricin | ClBzH | Me₂SO₄ | Methyl |
| 15 | AMB | ClBzH | Allyl Br | Allyl |
| 16 | AMB* | ClBzH | Me₂SO₄ | Methyl |
| 17 | AMB | Furaldehyde | Me₂SO₄ | Methyl |
| 18 | AMB | BrBzH | Me₂SO₄ | Methyl |

*Directly from fermentation Mycellium.

EXAMPLE 1

Amphotercin B Methyl Ester

To 15 mL of anhydrous DMF in a 25 mL flask was added p-chlorobenzaldehyde (0.278 g, 1.98×E-3 moles). While purging the flask with nitrogen, Amphotericin B (1.005 g, 1.01×E-3 moles) is slowly sifted into the vigorously stirred solution over 3 to 4 minutes. All the solid dissolved within 15 minutes and stirring was continued for an additional 15 minutes. At this point all the Amphotericin B was converted to the soluble N-p-chlorobenzylidine derivative.

To the clear yellow solution was added N,N-diisopropylethyl amine (1.75 mL, 1.01×E-2 moles) followed by methyl iodide (0.625 mL, 1.01×E-2 moles). After 45 minutes, a small aliquot of the reaction mixture was removed and analyzed by reverse phase HPLC. The analysis indicated no Amphotericin B was present in the reaction mixture. The major component of the product mixture was the corresponding methyl ester (93% area). Note that the benzylidine group hydrolyzes under the conditions of the analysis so only the free base is detected in the HPLC analysis.

The product, Amphotericin B methyl ester, was isolated as the Schiff base with p-chloro-benzaldehyde by adding the reaction mixture to 150 mL of methyl tertiary butyl ether. The yellow solid which precipitated was isolated by centrifugation and washed once with methyl tertiary butyl ether, twice with 5% aqueous sodium chloride and once with water affording after drying the Amphotericin B methyl ester (1.09 g) as a bright yellow solid.

EXAMPLE 2

Amphotericin B Methyl Ester

To 8.0 mL of anhydrous DMF in a 25 mL flask was added trimethylacetaldehyde (0.173 mL, 1.37×E-3 moles). While purging the flask with nitrogen, Amphotericin B (0.531 g, 5.37×E-4 moles) is slowly sifted into the vigorously stirred solution over 3 to 4 minutes. All the solid dissolved within 8 minutes and stirring was continued for an additional 30 minutes. At this point all the Amphotericin B was converted to the soluble N-t-butyl methine derivative.

To the clear yellow solution was added N,N-diisopropylethyl amine (0.740 mL, 4.25×E-3 moles) followed by methyl iodide (0.264 mL, 4.25×E-3 moles). The reaction mixture was allowed to stir overnight at ambient temperature and a small aliquot of the reaction mixture was removed and analyzed by reverse phase HPLC. The analysis indicated none of the parent Amphotericin B was present in the reaction mixture. The major component of the product mixture was the corresponding methyl ester. Note that the t-butyl methine group hydrolyzes under the conditions of the analysis so only the free base is detected in the HPLC analysis.

The product, Amphotericin B methyl ester, was isolated by adding the reaction mixture to 80 mL of methyl tertiary butyl ether. The yellow solid which precipitated was isolated by centrifugation and washed once with methyl tertiary butyl ether, twice with 5% aqueous sodium chloride and once with water affording after drying the Amphotericin B methyl ester (0.425 g) as a bright yellow solid.

EXAMPLE 3

Amphotericin B Methyl Ester

To 20 mL of anhydrous DMF in a 25 mL flask was added p-chlorobenzaldehyde (0.0866 g, 6.16×E-4 moles). While purging the flask with nitrogen, Amphotericin B (0.2023 g, 2.02×E-4 moles) is slowly sifted into the vigorously stirred solution over 3 to 4 minutes. All the solid dissolved within 15 minutes and stirring was continued for an additional 15 minutes. At this point all the Amphotericin B was converted to the soluble N-p-chlorobenzylidine derivative.

To the clear yellow solution was added N,N-diisopropylethyl amine (0.351 mL, 6.07×E-4 moles) followed by dimethyl sulfate (0.103 mL, 6.07×E-4 moles). The reaction mixture was allowed to stir for 20 minutes at ambient temperature and a small aliquot of the reaction mixture was removed and analyzed by reverse phase HPLC. The analysis indicated no unreacted Amphotericin B was present in the reaction mixture. The major component of the product mixture was the corresponding methyl ester (90% HPLC area @λ408 nm). After 35 minutes reaction, the mixture was added to 20 mL of methyl tert.-butyl ether and a yellow solid precipitated. The solid was isolated by centrifugation and washed once with 10 mL of methyl tert.-butyl ether. Washing with water and drying of the solid under high vacuum afforded Amphotericin B methyl ester (purity 92% by HPLC analysis).

EXAMPLE 4

Amphotericin B Methyl Ester

To 1.5 mL of anhydrous DMF in a 3 mL flask was added p-chlorobenzaldehyde (0.0663 g, 6.57×E-4 moles). While purging the flask with nitrogen, Amphotericin B (0.1511 g, 1.51×E-4 moles) is slowly sifted into the vigorously stirred solution over 3 to 4 minutes. All the solid dissolved within 15 minutes and stirring was continued for an additional 15 minutes. At this point all the Amphotericin B was converted to the soluble N-p-chlorobenzylidine derivative.

To the clear yellow solution was added diisopropylethyl amine (0.789 mL, 4.53×E-4 moles) followed by methyl p-toluenesulfonate (0.0843 g, 4.53×E-4 moles). The reaction mixture was allowed to stir for 22 hours at ambient temperature and a small aliquot of the reaction mixture was removed and analyzed by reverse phase HPLC. The analysis indicated no unreacted Amphotericin B was present in the reaction mixture. The major component of the product mixture was the corresponding methyl ester (90% HPLC area @$\lambda$408 nm). The mixture was added to 15 mL of methyl tert.-butyl ether and a yellow solid precipitated. The solid was separated by centrifugation and washed once with 10 mL of methyl tert.-butyl ether. Washing with water and drying under high vacuum afforded 0.138 g of Amphotericin B methyl ester.

EXAMPLE 5

Amphotericin B Methyl Ester

To 1.5 mL of anhydrous DMF in a 3 mL flask was added p-chlorobenzaldehyde (0.0747 g, 4.77×E-4 moles). While purging the flask with nitrogen, Amphotericin B (0.1511 g, 1.51×E-4 moles) is slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative.

To the clear yellow solution was added N,N-diisopropylethylamine (0.083 mL, 4.77×E-4 moles) followed by methyl methanesulfonate (0.041 mL, 4.77×E-4 moles). The reaction mixture was allowed to stir for 22 hours at ambient temperature and a small aliquot of the reaction mixture was removed and analyzed by reverse phase HPLC. The analysis indicated no unreacted Amphotericin B was present in the reaction mixture. The major component of the product mixture was the corresponding methyl ester. The mixture was added to 15 mL of methyl tert.-butyl ether and yellow solid precipitated. The solid was separated by centrifugation and washed once with 10 mL of methyl tert.-butyl ether. Washing with water and drying under high vacuum afforded 0. 177 g of Amphotericin B methyl ester.

EXAMPLE 6

Amphotericin B Alkyl Esters

Amphotericin B (0.301 g, 3.01×E-4 mole) was slowly sifted into a solution of trimethylacetaldehyde (0.098 mL, 9.03×E-4 mole) in 4.5 mL of dry DMF. After 10 minutes all the solid had dissolved, indicating complete conversion to the Schiff base. The solution was stirred for a total of 45 minutes. This stock solution was then utilized in the three experiments described below:

A. To 1.5 mL of the Schiff base solution described above was added N,N-diisopropylethylamine (0.126 mL, 2.41×E-4 mole) followed by iodoethane (0.019 mL, 2.41×E-4 mole). The resulting solution was stirred for 24 hours at ambient temperature. Analysis of the reaction mixture by HPLC indicated 78.6% of the ethyl ester of Amphotericin B and 5.9% unreacted Amphotericin B. The product was isolated by adding the reaction mixture to 15 mL of methyl tert.-butyl ether and centrifuging a yellow solid. The precipitate was washed once with 10 mL of the ether and dried.

B. To 1.5 mL of the Schiff base solution described above was added N,N-diisopropylethylamine ethylamine (0.126 mL, 2.41×E-4 mole) followed by 1-iodopropane (0.024 mL, 2.41×E-4 mole). The resulting solution was stirred for 24 hours at ambient temperature. Analysis of the reaction mixture by HPLC indicated 66.5% of the n-propyl ester of Amphotericin B and 23.0% unreacted Amphotericin B. The product was isolated by adding the reaction mixture to 15 mL of methyl tert.-butyl ether and centrifuging a yellow solid. The precipitate was washed once with 10 mL of the ether and dried.

C. To 1.1 mL of the Schiff base solution described above was added N,N-diisopropylethylamine (0.092 mL, 1.77×E-4 mole) followed by 1-iodobutane (0.020 mL, 0.77×E-4 mole). The resulting solution was stirred for 24 hours at ambient temperature. Analysis of the reaction mixture by HPLC indicated 49.9% of the butyl ester of Amphotericin B and 32.6% unreacted Amphotericin B. The product was isolated by adding the reaction mixture to 11 mL of methyl tert.-butyl ether and centrifuging a yellow solid. The precipitate was washed once with 8 mL of the ether and dried.

EXAMPLE 7

Amphotericin B Benzyl Ester

To 1.5 mL of anhydrous DMF in a 3 mL flask was added p-chlorobenzaldehyde (0.0245 g, 1.74×E-4 moles). While purging the flask with nitrogen, Amphotericin B (0.159 g, 1.59×E-4 moles) is slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative.

To the clear yellow solution was added N,N-diisopropylethylamine (0.083 mL, 4.77×E-4 moles) followed by benzyl chloride (0.055 mL, 4.77×E-4 moles) and 0.004 g of sodium iodide catalyst. The reaction mixture was allowed to stir for 4 days at ambient temperature and a small aliquot of the reaction mixture was removed and analyzed by reverse phase HPLC. The analysis indicated no unreacted Amphotericin B was present in the reaction mixture. The major component of the product mixture was the benzyl ester of Amphotericin B (67.7% HPLC area @$\lambda$408 nm). The mixture was added to 15 mL of methyl tert.-butyl ether and a yellow solid precipitated. The solid was separated by centrifugation and washed once with 10 mL of methyl tert.-butyl ether. Drying under high vacuum afforded 0.116 g of p-chlorobenzylidine Amphotericin B benzyl ester.

EXAMPLE 8

Amphotericin B Methyl Ester

To 1.5 mL of anhydrous DMF in a 3 mL flask was added p-chlorobenzaldehyde (0.0663 g, 4.72×E-4 moles). While purging the flask with nitrogen, Amphotericin B (0.1511 g, 1.51×E-4 moles) is slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative. To the clear yellow solution was added N,N-diisopropylethylamine (0.079 mL, 4.53×E-4 moles) followed by methyl p-toluenesulfonate (0.0843 g, 4.53×E-4 moles). The reaction mixture was allowed to stir for 22 hours at ambient temperature and a small aliquot of the reaction mixture was removed and analyzed by reverse phase HPLC. The analysis indicated no unreacted Amphotericin B was present in the reaction mixture. The major component of the product mixture was Amphotericin B methyl ester. The mixture was added to 15 mL of methyl tert.-butyl ether and a yellow solid precipitated. The solid was separated by centrifugation and washed once with 10 mL of methyl tert.-butyl ether. Drying under high vacuum afforded 0.184 g of p-chlorobenzylidine Amphotericin B methyl ester.

EXAMPLE 9

Amphotericin B Methyl Ester Acetate Salt

To 1.5 mL of anhydrous DMF in a 3 mL flask was added p-chlorobenzaldehyde (0.0866 g, 6.16×E-4 moles). While purging the flask with nitrogen, Amphotericin B (0.2023 g, 2.02×E-4 moles) is slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative.

To the clear yellow solution was added N,N-diisopropylethylamine (0.352 mL, 6.07×E-4 moles) followed by dimethyl sulfate (0.103 mL, 6.07×E-4 moles). The reaction mixture was allowed to stir for 22 hours at ambient temperature and a small aliquot of the reaction mixture was removed and analyzed by reverse phase HPLC. The analysis indicated no unreacted Amphotericin B was present in the reaction mixture. The major component of the product mixture was the corresponding methyl ester (89.5% HPLC area @λ408 nm). The mixture was added to 15 mL of methyl tert.-butyl ether and a yellow solid precipitated. The solid was separated by centrifugation and washed once with 10 mL of methyl tert.-butyl ether. Drying under high vacuum afforded 0.2577 g of N-p-chlorobenzylidine Amphotericin B methyl ester (purity 87.3% by HPLC analysis), a bright orange solid.

Water (10 mL) was added to the solid and acetic acid was added to adjust the pH of the solution to between 5 and 5.5. A small amount of insoluble solid (mostly p-chlorobenzaldehyde) was removed by centrifuging and the clear yellow aqueous supernatant layer was freeze dried under vacuum yielding 0.1801 g of the acetate salt of Amphotericin B methyl ester.

EXAMPLE 10

Amphotericin B Methyl Ester Hydrochloride Salt

To 2.0 mL of anhydrous DMF in a 3 mL flask was added p-chlorobenzaldehyde (0.0868 g, 6.18×E-4 moles). While purging the flask with nitrogen, Amphotericin B (0.1996 g, 2.00×E-4 moles) was slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative.

To the clear yellow solution was added diisopropylethylamine (0.104 mL, 5.99×E-4 moles) followed by dimethyl sulfate (0.057 mL, 4.77×E-4 moles). The reaction mixture was allowed to stir for 45 minutes at ambient temperature and a small aliquot of the reaction mixture was removed and analyzed by reverse phase HPLC. The analysis indicated no unreacted Amphotericin B was present in the reaction mixture. The major component of the product mixture was the corresponding methyl ester (90.6% HPLC area @λ408 nm).

The mixture was added to 20 mL of methyl tert.-butyl ether and a yellow solid precipitated. The solid was separated by centrifugation and washed once with 10 mL of methyl tert.-butyl ether. Drying under a nitrogen stream afforded N-p-chlorobenzylidine Amphotericin B methyl ester. To the solid was added water (15 mL) and acetic acid (0.020 mL) to a pH of 4. The insoluble materials were removed by centrifugation and the clear yellow aqueous solution was acidified to pH 2 by the addition of concentrated hydrochloric acid. Freeze drying of this solution afforded Amphotericin B methyl ester (0.1 565 g) as its hydrochloride salt.

EXAMPLE 11

Candicidin Methyl Ester

To 1.3 mL of anhydrous DMF in a 3 mL flask was added p-chlorobenzaldehyde (0.0273 g, 1.94×E-4 moles). While purging the flask with nitrogen, Candicidin (0.0571 g, 5.71× E-5 moles) is slowly sifted into the vigorously stirred solution over 3 to 4 minutes. All the solid dissolved within 15 minutes and stirring was continued for an additional 30 minutes. At this point all the Candicidin was converted to the soluble N-p-chlorobenzylidine derivative.

To the clear yellow solution was added N,N-diisopropylethylamine (0.010 mL, 5.71×E-5 moles) followed by methyl iodide (0.004 mL, 5.71×E-5 moles). The reaction mixture was allowed to stir for 22 hours at ambient temperature and a small aliquot of the reaction mixture was removed and analyzed by reverse phase HPLC. The analysis indicated no unreacted Candicidin was present in the reaction mixture. The analysis indicated several peaks in the region expected for the methyl esters and UV spectra confirmed the presence of the heptaene chromophore in each of the peaks. The methyl esters were isolated by precipitation from methyl t-butyl ether, washing with aqueous sodium chloride solution, centrifuging and drying the solid under high vacuum.

EXAMPLE 12

Nystatin Methyl Ester

To 1.1 mL of anhydrous DMF in a 3 mL flask was added trimethylacetaldehyde (0.025 mL, 2.13×E-4 moles). While purging the flask with nitrogen, Nystatin (0.07111 g, 7.68× E-5 moles) was slowly sifted into the vigorously stirred solution over 3 to 4 minutes. All the solid dissolved within 5 minutes and stirring was continued for an additional 30 minutes. At this point all the Nystatin was converted to the soluble trimethylacetaldehyde Schiff base. Diode array HPLC showed a single polyene peak with maxima at 292, 306 and 320 nm.

To the clear yellow solution was added diisopropylethylamine (0.107 mL, 6.14×E-4 moles) followed by methyl iodide (0.038 mL, 6.14×E-4 moles). The reaction mixture was allowed to stir for 22 hours at ambient temperature and a small aliquot of the reaction mixture was removed and analyzed by reverse phase HPLC. The analysis indicated no unreacted Nystatin was present in the reaction mixture. The analysis indicated several peaks in the region expected for the methyl esters and UV spectra confirmed the presence of the tetraene and diene chromophore in each of the major peaks. The methyl ester was isolated by precipitation from methyl t-butyl ether, washing with aqueous sodium chloride solution, centrifuging and drying the solid under high vacuum.

EXAMPLE 13

Pimaricin Methyl Ester

To 1.5 mL of anhydrous DMF was added p-chlorobenzaldehyde (0.0883 g, 6.28×E-4 moles). While purging the flask with nitrogen Pimaricin (0.1336 g, 2.01× E-6 moles) was slowly sifted into the stirring solution. The mixture was stirred for 1.5 hours at ambient temperature and diisopropylethylamine (0.105 mL, 6.00×E-4 moles) was added followed by dimethyl sulfate (0.057 mL, 6.00×E-4 moles). The mixture was stirred for 22 hours at ambient temperature and analyzed by diode array HPLC. The analysis indicated none of the starting Pimaricin remained and one major product, the corresponding methyl ester, was formed. The UV spectrum of this product was consistent with the tetraene chromophore with maxima at 265, 305 and 320 nm. The ester was isolated as in Example 12.

EXAMPLE 14

Partricin Methyl Ester

To 1.5 mL of anhydrous DMF was added p-chlorobenzaldehyde (0.0285 g, 2.03×E-4 moles). While purging the flask with nitrogen Partricin (0.0672 g, 5.73×E-5 moles) was slowly sifted into the stirring solution. The mixture was stirred for 1.5 hours at ambient temperature and diisopropylethylamine (0.030 mL, 1.72×E-4 moles) was added followed by dimethyl sulfate (0.016 mL, 1.72×E-4 moles). The mixture was stirred for 22 hours at ambient temperature and analyzed by diode array HPLC. The analysis indicated none of the starting Partricin remained and several major ester products were formed. The UV spectrum of each of these products was consistent with the Partricin chromophore with maxima at 360, 380 and 400 nm. The ester was isolated as in Example 13.

EXAMPLE 15

Amphotericin B Allyl Ester Acetate Salt

To 2.0 mL of anhydrous DMF in a 3 mL flask was added p-chlorobenzaldehyde (0.0893 g, 6.35×E-4 moles). While purging the flask with nitrogen, Amphotericin B (0.2030 g, 2.02×E-4 moles) is slowly sifted into the vigorously stirred solution over 3 to 4 minutes. All the solid dissolved within 15 minutes and stirring was continued for an additional 30 minutes. At this point all the Amphotericin B was converted to the soluble N-p-chlorobenzylidine derivative.

To the clear yellow solution was added N,N-diisopropylethylamine (0.106 mL, 6.09×E-4 moles) followed by allyl bromide (0.053 mL, 6.09×E-4 moles). The reaction mixture was allowed to stir for 22 hours at ambient temperature and a small aliquot of the reaction mixture was removed and analyzed by reverse phase HPLC. The analysis indicated no unreacted Amphotericin B was present in the reaction mixture. The major component of the product mixture was the corresponding allyl ester (76.0% HPLC area @$\lambda$408 nm). The mixture was added to 20 mL of methyl tert.-butyl ether and a yellow solid precipitated. The solid was separated by centrifugation and washed once with 10 mL of methyl tert.-butyl ether. Drying under a stream of air afforded N-p-chlorobenzylidine Amphotericin B allyl ester, a golden yellow solid. Water (10 mL) was added to the solid and acetic acid was added to adjust the pH of the solution to between 3.5 and 4.0. A small amount of insoluble solid (mostly p-chlorobenzaldehyde) was removed by centrifuging and the aqueous supernatant layer was freeze dried under vacuum yielding 0.1649 g of the acetate salt of Amphotericin B allyl ester.

EXAMPLE 16

Amphotericin B Methyl Ester Prepared Directly from Fermentation Mycelium

A sample of the fermentation mycelium (0.4923 g estimated to contain 0.0137 g, 1.37×E-5 mole, AMB by UV analysis) was added to a solution of p-chlorobenzaldehyde (0.0109 g, 7.75×E-5 mole) in 5 mL of anhydrous DMF. The mixture was sonicated for one hour, centrifuged and the clear supernatant liquid separated. Amphotericin B itself can be recovered from the supernatant by the addition of water, or converted to the methyl ester by the addition of 0.040 mL (2.30×E-4 mole) of N,N-diisopropylethylamine followed by methyl iodide (0.014 mL, 2.25×E-4 mole). Analysis of the reaction by HPLC after 30 minutes reaction indicated 47.7% Amphotericin B methyl ester and 32.5% unreacted AMB.

EXAMPLE 17

Amphotericin B Methyl Ester

Amphotericin B (0. 1022 g, 1.02×E-4 moles) was slowly added to a solution of 0.025 mL of furaldehyde (0.030 g, 3.07×E-4 mole) in 1.0 mL of anhydrous DMF. The resulting mixture was stirred for 45 minutes at room temperature. All solid dissolved at this point to form a clear amber solution containing the furaldehyde Schiff base. N,N-diisopropylethylamine (0.053 mL, 3.07×E-4 moles) and dimethyl sulfate (0.029 mL, 3.07×E-4 moles) were added and the resulting solution stirred for 30 minutes at room temperature.

A small aliquot of the reaction mixture was removed and analyzed by reverse phase HPLC. The analysis indicated no unreacted Amphotericin B was present in the reaction mixture. The major component of the product mixture was the corresponding methyl ester (88.3% HPLC area @$\lambda$408nm). The mixture was added to 10 mL of methyl tert.-butyl ether precipitating the furaldehyde Schiff base as a golden yellow solid. After isolation and drying, the yellow solid was added to 10 mL of water forming Amphotericin B methyl ester, a bright yellow solid.

EXAMPLE 18

Amphotericin B Methyl Ester

Amphotericin B (0.0549 g, 5.39×E-5 moles) was slowly added to a solution of 0.0299 g (1.62×E-4 moles) of p-bromobenzaldehyde in 0.55 mL of anhydrous DMF. The mixture was stirred for 30 minutes at room temperature at which point a clear amber solution had formed containing the p-bromobenzylidine derivative of Amphotericin B. N,N-diisopropylethylamine (0.028 mL, 1.62×E-4 moles) and dimethyl sulfate (0.015 mL, 1.62×E-4 moles) were added and the resulting solution stirred for 45 minutes at room temperature.

A small aliquot of the reaction mixture was removed and analyzed by reverse phase HPLC. The analysis indicated no unreacted Amphotericin B was present in the reaction mixture. The major component of the product mixture was the corresponding methyl ester (72.5% HPLC area @$\lambda$408 nm). The mixture was added to 7 mL of methyl tert.-butyl ether precipitating the p-bromobenzylidine derivative as a golden yellow solid. The yellow solid was isolated by centrifugation and dried.

What is claimed:

1. A process for preparing esters of polyene macrolide antibiotics comprising:

a) allowing a mixture containing an amphoteric polyene macrolide antibiotic selected from the group consisting of amphotericin A, amphotericin B, candicidin, nystatin, pimaricin, partricin, and their derivatives, and a solvent selected from the group consisting of dimethylformamide, dimethylacetamide, N-methyl-2- pyrrolidine, dimethyl sulfoxide, acyclic secondary amides, cyclic secondary amides, and dialkyl sulfoxides, to react with an aldehyde selected from the group consisting of aromatic, heterocyclic and aliphatic aldehydes to yield the corresponding imine derivative which imine derivative is soluble in a polar organic solvent selected from the group consisting of dimethyl sulfoxide, N,N-dimethylformamide, N,N-dimethylacetamide, and N-methyl-2-pyrrolidine;

b) esterifying said imine derivative by contacting said imine derivative with an alkylating agent selected from the group consisting of alkyl chlorides, alkyl bromides, alkyl iodides, aralkyl chlorides, aralkyl bromides, aralkyl iodides, dimethyl sulfate, diethyl sulfate, methyl methanesulfonate, methyl trifluoromethanesulfonate, methyl p-toluenesulfonate, methyl iodide, dimethyl sulfate, benzyl bromide, and methyl p-toluene-sulfonate in the presence of a hindered tertiary amine selected from the group consisting of N,N-diisopropylethylamine and 1,8-bis (dimethylamino-naphthalene) to yield the corresponding alkyl ester imine product; and c) contacting said alkyl ester imine product with water to convert said alkyl imine ester product to the polyene macrolide alkyl ester product.

2. The process according to claim 1 wherein the solvent of said solution is a polar organic solvent selected from the group consisting of acyclic and cyclic secondary amides and dialkyl sulfoxides.

3. The process according to claim 1 wherein the alkylating agent is selected from the group consisting of alkyl and aralkyl chlorides, bromides, and iodides.

4. The process according to claim 1 wherein the alkylating agent is selected from the group consisting of sulfates and sulfonates.

5. The process according to claim 4 wherein the sulfate is dimethyl sulfate.

6. The process according to claim 4 wherein the sulfonate is selected from the group consisting of diethyl sulfonate, methyl methanesulfonate, methyl trifluoromethanesulfonate and methyl p-toluenesulfonate.

7. The process according to claim 1 wherein the aldehyde is selected from the group consisting of benzaldehyde and substituted benzaldehydes.

8. The process according to claim 1 wherein the aldehyde is selected from the group consisting of acetaldehyde and substituted acetaldehydes.

9. The process according to claim 1 wherein the aldehyde is selected from the group consisting of furaldehyde and substituted furaldehydes.

10. The process according to claim 1 wherein the alkylating agent is methyl iodide.

11. The process according to claim 1 wherein the alkylating agent is dimethyl sulfate.

12. The process according to claim 1 wherein the alkylating agent is benzyl bromide.

13. The process according to claim 1 wherein the alkylating agent is methyl p-toluene-sulfonate.

14. The process according to claim 1 wherein the hindered tertiary amine is selected from the group consisting of N,N-diisopropylethylamine and 1,8-bis(dimethylamino-naphthalene).

15. The process according to claim 1 wherein the solvent is dimethylformamide.

16. The process according to claim 1 wherein the solvent is dimethylacetamide.

17. The process according to claim 1 wherein the solvent is N-methylpyrollidone-2-pyrrolidone.

18. The process according to claim 1 wherein the solvent is dimethyl sulfoxide.

19. The process according to claim 1 wherein the said resulting polyene macrolide ester product is optimally recovered from the reaction mixture by at least one of centrifugation, precipitation or extraction.

20. The process according to claim 1 wherein the amphoteric polyene macrolide is extracted directly from the fermentation product mixture without isolation, and esterified according the process of claim 1.

21. The process according to claim 1 wherein said amphoteric polyene macrolide antibiotic comprises Amphotericin B.

22. The process according to claim 1 wherein said amphoteric polyene macrolide antibiotic comprises Candicidin.

23. The process according to claim 1 wherein said amphoteric polyene macrolide antibiotic comprises Nystatin.

24. The process according to claim 1 wherein said amphoteric polyene macrolide antibiotic comprises Pimaricin.

25. The process according to claim 1 wherein said amphoteric polyene macrolide antibiotic comprises Partricin.

* * * * *